United States Patent [19]

Gatti

[11] Patent Number: 4,634,702

[45] Date of Patent: Jan. 6, 1987

[54] QUINOXALINEMETHANOL COMPOUNDS FOR COMBATTING SWINE DYSENTERY AND AS GROWTH PROMOTING FACTORS, METHOD OF PREPARATION, AND COMPOSITIONS CONTAINING THEM

[76] Inventor: Daniele Gatti, Via Sacco & Vanzetti, 3, 27020 Travacò Siccomario, Italy

[21] Appl. No.: 662,836

[22] Filed: Oct. 19, 1984

[30] Foreign Application Priority Data

Nov. 7, 1983 [IT] Italy ................................ 23605 A/83

[51] Int. Cl.$^4$ ................. C07D 241/52; A61K 31/495
[52] U.S. Cl. ..................................... 514/249; 544/353
[58] Field of Search ........................ 544/353; 514/249

[56] References Cited

U.S. PATENT DOCUMENTS 4,303,657 12/1981 Young et al. ........................ 544/353
4,373,100 2/1983 Benko ................................. 544/353

OTHER PUBLICATIONS

Padeiskaya et al., Chem. Abs., 68, 11326s (1968).

Primary Examiner—Mark L. Berch
Attorney, Agent, or Firm—Stevens, Davis, Miller & Mosher

[57] ABSTRACT

The invention relates to new compounds useful for combatting swine dysentery, endowed with growth promoting action but devoid of mutagenic action.

Furthermore, the invention relates to the method for the preparation of the compounds of the invention and to compositions containing them.

4 Claims, No Drawings

QUINOXALINEMETHANOL COMPOUNDS FOR COMBATTING SWINE DYSENTERY AND AS GROWTH PROMOTING FACTORS, METHOD OF PREPARATION, AND COMPOSITIONS CONTAINING THEM

This invention relates to compounds useful for combatting swine dysentery, endowed with growth promoting action, but devoid of mutagenic action.

Another object of the present invention is the method for the preparation of the compounds of the invention as well as the compositions containing them.

Swine dysentery, also known as vibrionic dysentery or hemorragic dysentery, is an enteric disease primarily characterized by muco-hemorragic diarrhear with large intestine lesions. It is known that *Treponema hyodysenteriae* is the etiologic agent involved with the swine dysentery. Hitherto, swine dysentery was combatted by constant feeding of antibacterial agents with therapy based on the use of high doses of the above mentioned drugs. However, drugs hitherto used, even when administered at abnormally high doses did not give the desired results.

U.S. Pat. No. 4,086,345 discloses and claims quinoxaline derivatives useful for treating swine dysentery and U.S. Pat. No. 4,128,642 discloses and claims the above compounds as growth rate increasing factors. However, the compounds disclosed in the above mentioned patents are endowed with mutagenic action. Therefore, the use of the above mentioned quinoxaline derivatives is prohibited in some countries, whereas they are tolerated in other countries. As known as men eat the meat of animals treated with the above mentioned quinoxaline derivatives, there is an undoubted risk for animals and men, because of the mutagenic action of those compounds.

Another risk exists for ecology in that waste materials from breedings contain mutagenic compounds.

Therefore, there was a continuing need for drugs of low toxicity and high potence against *Treponema hyodysenteriae*, but devoid of mutagenic action when tested by the conventional Ames test (see the well known "Handbook of Mutagenicity Test Procedures", Ed. Kibey et al, Elsevier/North Holland Biochemical Press, 1977).

It has been now found that the compounds of the general formula (I):

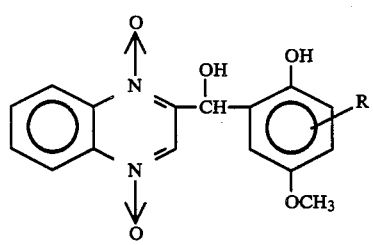

(wherein R is H or a 1-4 C alkyl group) are efficacious against *Treponema hyodysenteriae*, have a growth promoting action, but are wholly devoid of mutagenic action.

In particular, the compound of formula (I) wherein R=H, the quinoxalyl-$N^1,N^4$-dioxide-2-hydroxy-5-methoxy-phenylcarbinol, is of a low order toxicity and shows a clearly specific action against *Treponema hyodysenteriae*. Such a specific action is very important in that allows the prophylatic administration of this compound, in that it does not change the intestinal flora. Furthermore, it is an effective growth promoting factor. Quinoxalyl-$N^1,N^4$-dioxide-2-hydroxy-5-methoxy-phenylcarbinol will be indicated hereafter as G 8 compound.

Another object of the present invention is the method for the preparation of the compounds comprised in the general formula (I), by reacting 2-quinoxaline-carboxyaldehyde-$N^1,N^4$-dioxide with 4-methoxyphenolmagnesium chloride, optionally substituted. The reaction occurs in an apolar solvent, at room temperature, the molar ratio of the two reagents being 1:1.

The compounds of this invention can be administered by oral route incorporated in the feed ration. They can be intimately mixed with a generally used swine feed ration, to prepared a homogeneous feed ration. The term "feed ration" in this invention is intended to mean the food for the swine and it is not intended that the invention is limited thereby. Preferably, a compound according to the present invention is thoroughly mixed with the feed ration so that it is uniformly dispersed throughout. It is also possible to sprinkle it on the daily food supplies in the form of a powder or as pellets.

The amount of the compound to be added to swine feed rations is generally comprised between 25 and 500 g/ton.

Compound G 8 has been tested "in vitro" against *Treponema hyodysenteriae* by a known technique. The minimum inhibitory concentration (the lowest concentration of compound in a dilution series where growth is inhibited) was 0.1 μg/ml.

The minimum bacteriocidal concentration (the lowest concentration of compound in which no viable Treponemes are observed upon dilution and subculture from the broth onto blood agar plates) was greater than 0.1 μg/ml but less than 1 μg/ml.

Furthermore, G8 compound was tested for acute toxicity by several modes of administration in four species, namely mouse, rat, guinea pig and rabbit. The compound was found to be of low order of toxicity. The test results are given below in tables 1, 2, 3 and 4.

TABLE 1

| Dosage mg/kg | Acute toxicity of G 8 in female mice Dead/Treated animals after | | | |
|---|---|---|---|---|
| | 1 day | 2 days | 4 days | 7 days |
| | Endoperitoneal administration | | | |
| 2000 | 6/6 | | | 6/6 |
| 1000 | | 6/6 | | 6/6 |
| 500 | | | | 6/12 |
| 250 | | | | 0/18 |
| | Oral administration | | | |
| 0ˣ | | | | 0/6 |
| 4000 | | | 1/12 | 1/12 |
| 2000 | | | | 0/12 |
| 1000 | | | | 0/12 |

ˣonly the vehicle

TABLE 2

Acute Toxicity of G 8 in the Rat a. First Experiment

TABLE 2-continued

Acute Toxicity of G 8 in the Rat

| Sex | Route of Administration | mg/kg | Dead/Treated within 21 days | Body Weight in g. Start | (m ± SEM) Termination | Statistical Significance* |
|---|---|---|---|---|---|---|
| M | oral | 4000 | 0/4 | 234.5 ± 13.8 | 288.7 ± 13.8 | t 0.05 |
| M | oral | 0ˣ | 1/4 | 233.7 ± 3.7 | 331.0 ± 0.5 | |
| F | oral | 4000 | 0/4 | 201.2 ± 4.2 | 238.2 ± 12.1 | t 0.05 |
| F | oral | 0ˣ | 1/4 | 189.2 ± 3.9 | 230.0 ± 10.5 | |
| M | endoperitoneal | 500 | 1/4 | 234.0 ± 6.2 | 314.3 ± 10.3 | t 0.05 |
| M | endoperitoneal | 0ˣ | 0/4 | 230.0 ± 5.7 | 324.0 ± 8.7 | |
| F | endoperitoneal | 500 | 2/4 | 206.2 ± 8.7 | 286.0 − 272.0 | t 0.05 |
| F | endoperitoneal | 0ˣ | 0/4 | 207.5 ± 4.3 | 253.5 ± 7.7 | | b. Second experiment

| Sex | Route of Administration | mg/kg | Dead/Treated within 7 days | Body weight in g. Start | (±SE) Termination |
|---|---|---|---|---|---|
| M | oral | 4000 | 0/4 | 222.5 ± 6.2 | 231.7 ± 15.7 |
| F | oral | 4000 | 0/4 | 252.0 ± 16.6 | 253.5 ± 12.1 |
| M | intraperitoneal | 500 | 2/4 | 226.2 ± 6.8 | 225.0 − 212 |
| F | intraperitoneal | 500 | 0/4 | 232.5 ± 5.9 | 218.2 ± 7.0 | c. Cumulative data regardless of animal sex

| Route of administration | mg/kg | Dead/Treated within 7 days |
|---|---|---|
| Oral | 0ˣ | 0/8 |
| oral | 4000 | 0/16 |
| intraperitoneal | 0ˣ | 0/8 |
| intraperitoneal | 500 | 4/16 |

ˣOnly the vehicle was administered by the same route
*Student's t test

TABLE 3

Acute toxicity of G 8 in the guinea pig by oral administration

| Dosage mg/kg | Dead/Treated within 21 days |
|---|---|
| 500 | 0/4 |
| 1000 | 1/4 |
| 2000 | 5/6 |
| 4000 | 6/6 |
| 0ˣ | 0/13 |

ˣOnly the vehicle was administered

TABLE 4

Acute toxicity of G 8 in the rabbit by esophageal administration

| Dosage mg/kg | Dead/Treated within 7 days | Body weight in g. Start | (m ± SE) Termination |
|---|---|---|---|
| 2000 | 0/2 | 2250−2150 | 2180 + 2140 |
| 1000 | 0/4 | 2037 ± 104.3 | 1922.5 ± 71.5 |
| 0ˣ | 0/4 | 2135 ± 75 | 2262 ± 215 |
| 500 | 0/2 | 2000−2100 | 1650−1550 |

ˣOnly the vehicle was administered

In view of the favorable acute toxicity data, compound G 8 was administered orally in sub-acute, but relatively large doses, to mice and rats for 15 days. Results are given in Tables 5 and 6.

TABLE 5

Subacute toxicity of G 8 in the mouse

Daily dose: 500 mg. G 8 by gastric gavage for 15 days

| Oral treatment | Dead/Treated | % Body weight change (m ± SE) | Fresh organ to body weight ratio Liver | Kidneys |
|---|---|---|---|---|
| Vehicle | 0/10 | 20.4 ± 4.2 | 5.2 ± 0.2 | 1.4 ± 0.1 |
| G 8, 500 mg/kg/day | 0/10 | −8.1 ± 3.9 | 5.9 ± 0.3 | 1.5 ± 0.1 | a. Mortality and body weight

Daily dose: 1 g/kg/day for 15 days

| Oral treatment | Dead/Treated | % Body weight change |
|---|---|---|
| Vehicle (H₂O) | 0/12 | 24.54 ± 0.64 |
| G 8 in water, 1 g/kg/day | 2/12 | 18.5 ± 0.75 |
| Vehicle (adraganth gum) (x) | 0/12 | 25.04 ± 1.18 |
| G 8 in adraganth gum | 3/12 | 16.27 ± 1.31 | b. SGOT and SGPT (24 hrs. after last dose)

| | Units/ml | |
|---|---|---|
| Oral treatment | SGOT | SGPT |
| Vehicle: | | |
| Water | 116 | 4 |
| Adraganth gum | 119 | 6 |
| G 8 in water | 124 | 9 |
| G 8 in adraganth gum | 132 | 10 |

TABLE 6

Subacute toxicity of G 8 in female rats

Daily dose: 22 g/kg/day of G 8 in female rats by gastric gavage for 21 days

TABLE 6-continued

| Oral treatment | Dead/ Treated | Body weight in g (m ± SE) | |
|---|---|---|---|
| | | Start | Termination |
| Vehicle | 2/6[x] | 200.0 ± 4.1 | 233.2 ± 5.1 |
| G 8, 2 g/kg/day | 1/6[x] | 204.1 ± 2.0 | 210.6 ± 9.6 |

Daily dose: 2 g/kg/day of G 8 by gastric gavage for 21 days

| Oral Treatment | Average percent weight of fresh organs (m ± SE) | | |
|---|---|---|---|
| | Lung | Liver | Kidneys |
| Vehicle (3 animals) | 0.85 ± 0.06 | 3.45 ± 0.07 | 0.95 ± 0.04 |
| G 8 (5 animals) | 1.08 ± 0.09 NS | 4.54 ± 0.10 | 1.04 ± 0.3 NS |

[x]Death caused by a mistake in esophagus incannalulation. Diagnosis was confirmed at the postmortem examination Chronic toxicity has been studied in female mice. Results were very satisfactory.

Furthermore, teratogenetic study was conducted with male and female mice and rats. The number of young delivered live at birth was comparable with controls. No malformations in either group were observed.

The compositions containing swine feed ration and as active ingredient, an effective dose of a compound comprosed in the general formula (I) are a further object of the present invention.

The compositions according to the present invention may be in form of powders or pellets.

The following examples are given to illustrate the present invention, without limiting it in any way.

EXAMPLE 1

A solution of 400 ml (1 mol) of methylmagnesium chloride in 600 ml of tetrahydrofuran is added dropwise with 124 g (1 mol) of 4-methoxyphenyl in 100 ml of tetrahydrofuran, under nitrogen and while keeping the temperature under 15° C.

2000 ml of benzene are then added and the solution is then concentrated, under a 15–20 mm vacuum, to about 2200 ml.

190 g (1 mol) of 2-quinoxaline-carboxyaldehyde-$N^1,N^4$-dioxide in 1000 ml of benzene are then added to the above concentrated solution and the mixture is kept under stirring overnight, at room temperature.

After having neutralized with 10% hydrochloric acid, the aqueous phase is discarded and the organic phase is evaporated under a 15–20 mm vacuum. By crystallization from acetone and decoloration with activated coal, there are obtained 156 g of the desired product. Yield 50% on the theoric. m.p. 138°–140° (dec.).

The elemental analysis gave the following results: (%)

| | Calculated | Found |
|---|---|---|
| C | 61.34 | 61.25 |
| H | 4.18 | 4.21 |
| N | 8.34 | 8.36 |

IR and NMR spectra confirm the foreseen structure.

EXAMPLE 2

Compound G 8 is mixed with swine feed rations at a level of 200 g/ton and was fed to swine housed in an area where there has been a previous outbreak of swine dysentery. Another herd was housed in a similar area, where there has been a previous outbreak of dysentery. They were fed the same rations as the first herd, but with no G 8 or other drug.

Many members of the herd developed symptoms of dysentery. G 8 was then added with the rations at a level of 400 g/ton. The spread of the disease was halted and the diseased members became free from dysentery symptoms.

EXAMPLE 3

The effect of compound G 8 was tested in feed rations for baby-swines.

Compound G 8 was added at a dosage level of 100 g/ton of feed. Five replicate groups of 10 animals (5 males and 5 females), age one day, were fed the ration containing G 8 and compared to 5 replicate groups of animals (5 males and 5 females) which received the same ration but without G 8.

The test period was 28 days. The results obtained are given in the following table:

| | Body weight gain/swine | |
|---|---|---|
| | Ration without G 8 | Ration with G 8 |
| Males | 6150 g | 6480 g |
| Females | 5740 g | 5880 g |
| Combined average | 6000 | 6190 |
| Improvement, % | — | 3.1 |
| Feed/gain ratio | 1.82 | 1.77 |
| Improvement, % | — | 2.8 |

I claim:

1. A compound for combatting swine dysentery, endowed with growth promoting action, but devoid of mutagenic action when tested by the conventional Ames test, and having the formula (I):

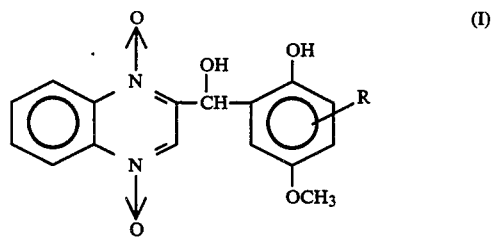

wherein R is H or a 1–4 C alkyl group.

2. Alpha(2-hydroxy-5-methoxy phenyl)quinoxaline-2-methanol, $N^1N^4$ dioxide.

3. A swine feed composition comprising a nutritional swine feed and as active ingredient a compound of claim 1, in an amount between 25 and 500 g/ton.

4. A growth promoting factor comprising as active ingredient a compound of the formula (I) of claim 1, in association with a pharmaceutically acceptable carrier.

* * * * *